United States Patent [19]

Curtis et al.

[11] Patent Number: 4,958,751
[45] Date of Patent: Sep. 25, 1990

[54] SUB-GINGIVAL MEDICAMENT APPLICATOR

[75] Inventors: John P. Curtis, Bloomsbury; James H. Kemp, Piscataway, both of N.J.

[73] Assignee: Colgate-Palmolive Company, New York, N.Y.

[21] Appl. No.: 338,259

[22] Filed: Apr. 14, 1989

[51] Int. Cl.⁵ .................... B67D 1/07; A61M 37/00; A61M 31/00
[52] U.S. Cl. .................... 222/192; 222/399; 222/527; 239/589.1; 401/190; 433/80; 604/147; 604/275
[58] Field of Search ............. 222/399, 192, 527, 538; 401/190; 239/590.5, 590, 589, 589.1; 604/140, 147, 148, 275; 433/80

[56] References Cited

U.S. PATENT DOCUMENTS 3,104,663  9/1963  Laws .................... 604/275 X
3,186,645  6/1965  Eberlein ................ 604/275 X
3,490,657  1/1970  Williams et al. ............ 222/399
3,561,433  2/1971  Kovach .................. 604/140 X
3,738,006  6/1973  Lopez et al. .............. 433/80 X
3,998,386 12/1976  Viets et al. ............ 239/589.1 X
4,411,623 10/1983  Axelsson ................... 433/80
4,562,867  1/1986  Stouffer ............... 239/589.1 X
4,742,963  5/1988  Marvaldi ................ 239/590.5

FOREIGN PATENT DOCUMENTS 1319051  4/1962  France .................... 401/190

Primary Examiner—Andres Kashnikow
Assistant Examiner—Gregory L. Huson
Attorney, Agent, or Firm—Norman Blumenkopf; Murray M. Grill; Robert C. Sullivan

[57] ABSTRACT

A sub-gingival medicament applicator comprising an aerosol container having a gingival medicament filling and a nitrogen propellant. A wand is secured to the container and has an end portion extending angularly to the rest thereof. The wand has a passageway therethrough. A valve, provided with an actuator, is provided for controlling fluid flow through a passageway in the wand to permit application of the medicament through the end piece onto the gums of the user in a manner for optimum benefit.

3 Claims, 1 Drawing Sheet

SUB-GINGIVAL MEDICAMENT APPLICATOR

BACKGROUND OF THE INVENTION

1. FIELD OF THE INVENTION

This invention relates to medicament applicators and, more particularly, to an aerosol type applicator especially adapted to apply gingival medicament to a patient.

2. DESCRIPTION OF THE PRIOR ART

Gingival medicaments are normally applied topically, usually with a brush or swab. Spray devices have not been found satisfactory because of lack of control for effective application in precise areas in the mouth of the user/patient, while also often subjecting a patient to staining of their clothes.

The present invention overcomes the disadvantages of the prior devices by providing for a convenient hand-held aerosol applicator having an end piece extending at an angle to the rest of the applicator to provide for easier access to the location being treated with no visual obstruction.

SUMMARY OF THE INVENTION

This invention relates to a hand-held sub-gingival medicament applicator, which includes an aerosol container which is charged with a filling of a gingival medicament in fluid form and a propellant of nitrogen. Attached to the container is a wand having an end piece extending angularly to the rest of the applicator. The wand has a passageway therethrough. A valve controlling fluid flow from the container into the passageway is provided. The container is hand held and is provided with an actuator for operating the valve. The passageway extending through the end piece may be tapered and a baffle may be provided to cooperate with the shape of the end piece and its passageway and exit port to cause vibration of the end piece, pulsation of dispensing or exiting fluid, or both.

DETAILED DESCRIPTION OF THE INVENTION

Figure 1:
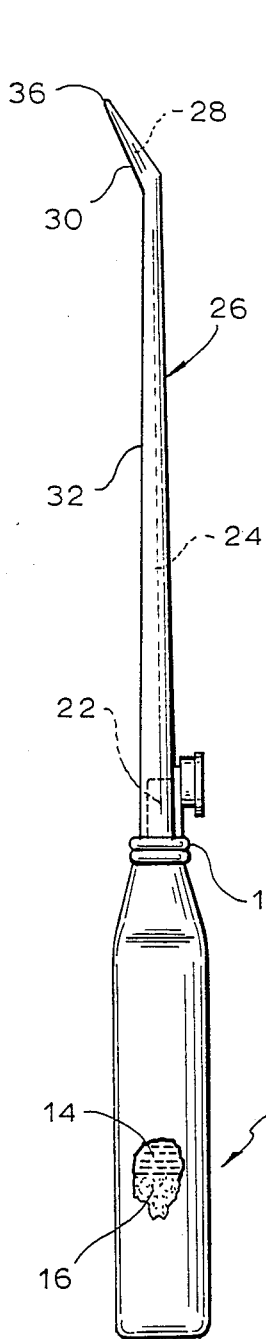
FIG. 1 is an elevational view of the sub-gingival medicament applicator according to the present invention.

With continuing reference to the accompanying drawing, and initially to FIG. 1, reference numeral 10 generally designates the sub-gingival medicament applicator in accordance with the present invention.

The applicator 10 includes an aerosol container 12 charged with a filling of a fluid gingival medicament 14 and a propellant 16 of nitrogen. The container 12 is provided with a valve 18 controlled by an actuator 20 for permitting fluid flow.

The container 12 is sized to fit in an average-size palm of the hand of the user and the actuator is, preferably, located and shaped for easy manipulation by the thumb of the user.

The container 12 has a discharge 22 opening into the passageway 24 of a wand 26 which is attached to the container 12. The wand may be made of synthetic plastic material or of a suitable sterilizable metal and either the wand or the container 12 may be disposable and replaceable.

Alternatively, the wand 26 may be permanently affixed to the container 12.

The wand 26 and the container 12 may be separated for refill of the container 12 and for washing or sterilization of the wand 26.

Figure 2:
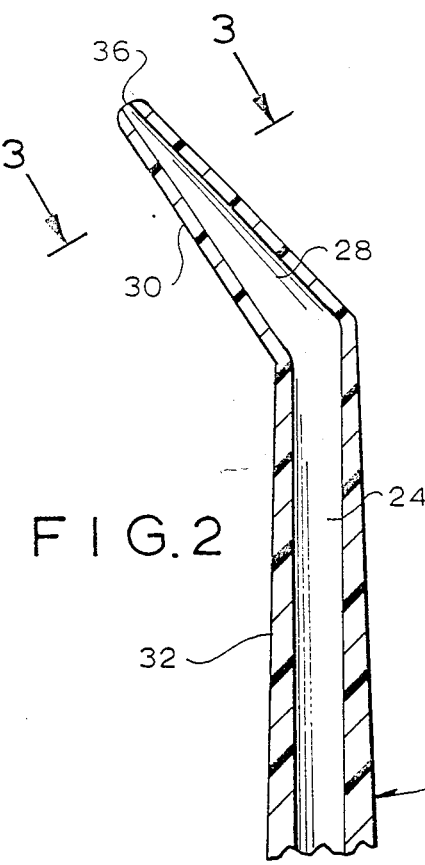
FIG. 2 is a longitudinal sectional view through a portion of the wand.
Figure 3:
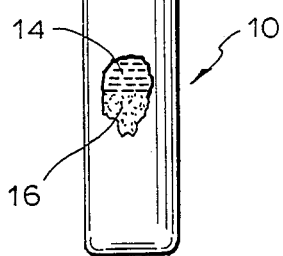
FIG. 3 is a sectional detail view taken along the plane of line 3—3 in FIG. 2; and, FIG. 4 is a sectional view, similar to FIG. 3, of a modified form of the invention.

Referring now to the construction of the wand 26, as particularly shown in FIGS. 2 and 3, the wand 26 has an end piece 30, which extends angularly with respect to the remaining shaft portion 32 of the wand 26. It has been found that the end portion makes, preferably, an obtuse angle with the shaft of from 135° to 160° and, most preferably, of 150° to the shaft 32. The passageway portion 28 within the end piece is, preferably, tapered to its exit port 36. The tapering configuration of the passageway portion 28 may be such as to cause pulsations of the dispensing or exiting fluid and/or vibration of the end piece 30.

Figure 4:
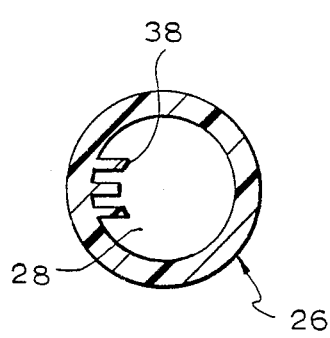

Alternatively, as shown in FIG. 4, a baffle 38, of selected shape, may be used to cause pulsations of the dispensing or exiting fluid medicament and/or vibration of the end piece 30 to enhance application of the gingival medicament.

It is to be noted that the shaft portion of the wand may be far more rigid than the end piece to facilitate application to the area desired to be medicated.

What is claimed is:

1. A sub-gingival medicament applicator comprising an aerosol container having a filling of gingival medicament and a non-toxic propellant, said container having an outlet opening and a valve for controlling fluid flow through said opening, actuator means on said container for said valve, and a wand secured to said container in alignment with said opening, said wand having a flexible end piece having a discharge port, and said wand having a passage therethrough from said opening to said port, and means in said end piece to cause vibration thereof.

2. A sub-gingival medicament applicator comprising an aerosol container having a filling of gingival medicament and a non-toxic propellant, said container having an outlet opening and a valve for controlling fluid flow through said opening, actuator means on said container for said valve, and a wand secured to said container in alignment with said opening, said wand having a flexible end piece having a discharge port, and said wand having a passage therethrough from said opening to said port, said end piece extending angularly with respect to the rest of said wand, said wand having a main shaft portion substantially more rigid than said end piece, said end piece being provided with means for causing vibration thereof as said fluid passes therethrough.

3. A sub-gingival medicament applicator comprising an aerosol container having a filling of gingival medicament and a non-toxic propellant, said container having an outlet opening and a valve for controlling fluid flow through said opening, actuator means on said container for said valve, and a wand secured to said container in alignment with said opening, said wand having a flexible end piece having a discharge port, and said wand having a passage therethrough from said opening to said port, said end piece extending angularly with respect to the rest of said wand, said wand having a main shaft portion substantially more rigid than said end piece, said end piece being provided with means to cause vibration of fluids passing therethrough.

* * * * *